United States Patent [19]

Paley

[11] 4,046,479
[45] Sept. 6, 1977

[54] REMOVABLE LOCKING CONNECTOR FOR LUER FITTINGS

[76] Inventor: Hyman W. Paley, 20 Broadmoor Drive, San Francisco, Calif. 94132

[21] Appl. No.: 679,835

[22] Filed: Apr. 23, 1976

[51] Int. Cl.² ............................................. B25G 3/00
[52] U.S. Cl. .............................. 403/306; 128/218 N; 285/391
[58] Field of Search ................ 403/47, 306, 341, 342, 403/343; 285/391, 175, 332; 128/221, 218 N

[56] References Cited

U.S. PATENT DOCUMENTS

| 1,372,238 | 3/1921 | Kreiter | 285/391 X |
| 1,793,068 | 2/1931 | Dickinson | 128/221 |
| 2,169,371 | 8/1939 | Payne | 128/221 |
| 2,370,718 | 3/1945 | Couse | 403/342 X |

Primary Examiner—Wayne L. Shedd
Attorney, Agent, or Firm—Flehr, Hohbach, Test, Albritton & Herbert

[57] ABSTRACT

Removable connector for locking Luer fittings together, comprising a cylindrical sleeve having internal threads toward the ends thereof for engaging external threads on male and female Luer fittings. In one particularly preferred embodiment, the internal thread for receiving the female fitting is substantially coarser than the internal thread for receiving the male fitting, and the thread on the female fitting is an interrupted thread. The connector sleeve can be mounted on the male fitting, and the female fitting can then be quickly connected or disconnected by a small turn of the female fitting.

6 Claims, 3 Drawing Figures

U.S. Patent
Sept. 6, 1977
4,046,479
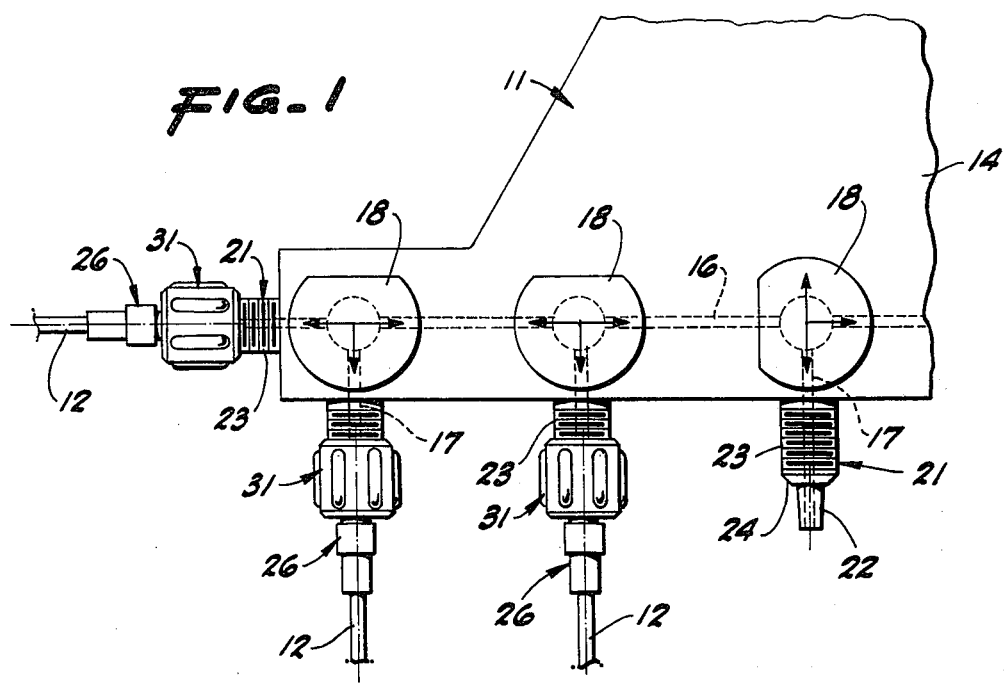
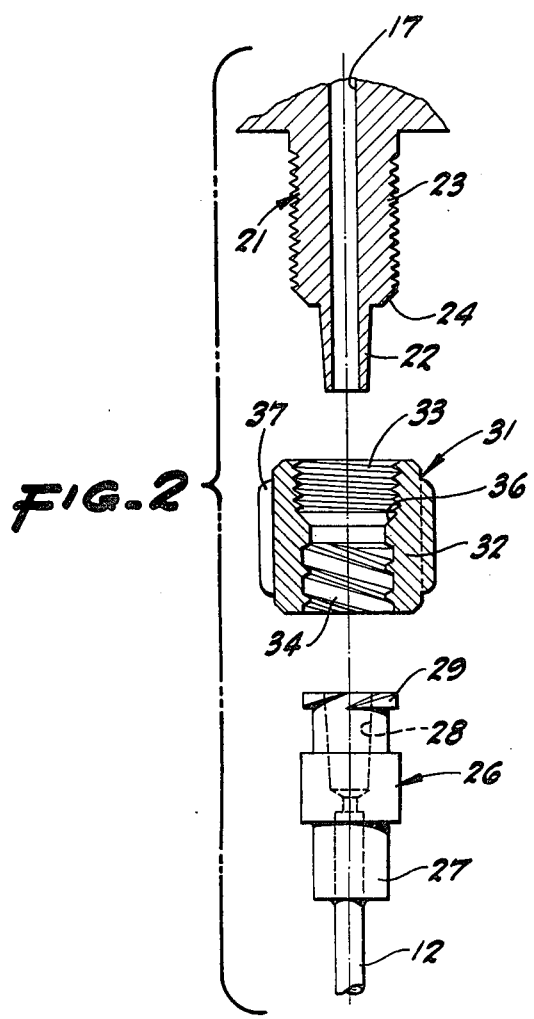
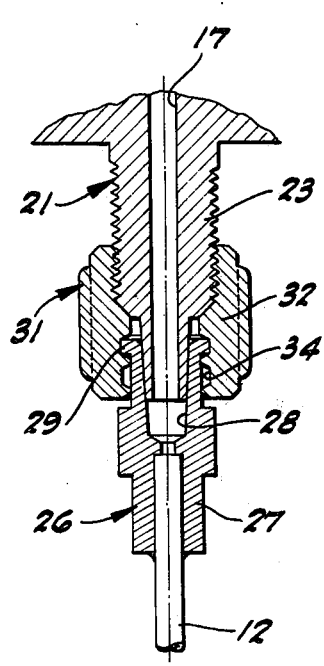

4,046,479

REMOVABLE LOCKING CONNECTOR FOR LUER FITTINGS

BACKGROUND OF THE INVENTION

This invention pertains generally to medical appliances and more particularly to a removable connector for locking Luer fittings together.

Luer fittings are used to provide leakproof connections between medical appliances or equipment such as flow control manifolds and catheters, hypodermic syringes and needles and the like. Luer connections generally consist of a male fitting having a tapered tip and a female fitting having a tapered bore for receiving the tapered tip in mating relationship. Such fittings are advantageous in that they provide accurate alignment between the parts, yet permit the parts to be separated readily. In order to prevent undesired separation of the parts, some Luer fittings have been provided with mating threads.

SUMMARY AND OBJECTS OF THE INVENTION

This invention provides a removable locking connector for Luer fittings, which can be engaged or disengaged quickly and easily to connect or separate the parts. The connector comprises a cylindrical sleeve having internal threads toward the ends thereof for engaging external threads on the male and female fittings. In one particularly preferred embodiment, the thread for the female fitting is substantially coarser than the thread for the male fitting and is formed by flanges defining an interrupted thread. This connector sleeve can be mounted on the male fitting, and the female fitting can then be quickly connected or disconnected by a small turn of the female fitting.

It is in general an object of the invention to provide a new and improved connector for locking Luer fittings together.

Another object of the invention is to provide the connector of the above character which is removable and can be utilized for connecting a wide variety of appliances together.

Another object of the invention is to provide the connector which permits the Luer fittings to be quickly and easily connected and separated.

Another object of the invention is to provide the connector of the above character which is particularly suitable for use with manifolds and catheters.

Additional objects and features of the invention will be apparent from the following description in which the preferred embodiment is set forth in detail in conjunction with the accompanying drawings.

BRIEF DESCRIPTION OF THE DRAWINGS

FIG. 1 is a fragmentary plan view of one embodiment of a manifold assembly incorporating the invention.

FIG. 2 is an exploded view, partly in cross-section, of a connector assembly according to the invention.

FIG. 3 is a center line sectional view of the connector assembly of FIG. 2, illustrating the Luer fittings in mating relationship.

DESCRIPTION OF THE PREFERRED EMBODIMENT

In the drawings, the invention is illustrated in conjunction with a manifold assembly 11 to which a plurality of catheters 12 are connected. The manifold assembly can, for example, be of the type described in copending appplication Ser. No. 579,906, filed May 22, 1975. Briefly, the manifold includes a body 14 having a longitudinally extending flow passageway 16 and a plurality of laterally extending flow passageways 17 formed therein. Valve members 18 are rotatably mounted in the manifold body at the intersections of the flow passageways for controlling communication between the passageways. It will be understood, however, that the invention is not limited to manifolds and catheters and that it can be utilized with a wide variety of other appliances.

Male Luer fittings 21 are provided at the edges of manifold body 14 in alignment with passageways 16, 17. Each of the fittings includes a tapered tip 22 through which the passageway extends an an external thread 23 at the base of the tip. As illustrated, the threaded portion of the fitting is of larger diameter than the tip portion, and a conical shoulder 24 is formed between the tip and the thread. The tip is formed with a standard Luer taper of 0.060 inch per inch, and in the preferred embodiment the tip is 0.25 inch long, 0.170 inch in diameter at the base, and 0.155 inch in diameter at the outer end.

Each of the catheters 12 has a female Luer fitting 26 affixed to one end thereof. Each of these fittings includes a body 27 in which an axially extending tapered bore 28 is formed. The taper of the bore 28 is a standard Luer taper, and the dimensions of the bore correspond to the dimensions of tip 22, whereby the bore is adapted to receive the tip in mating relationship.

Female fitting 26 also includes an external thread 29 toward the end of body 27 away from catheter 12. In the preferred embodiment, thread 29 is formed by flanges defining an interrupted thread of substantially coarser pitch than thread 23 and can be quickly engaged with or disengaged from a mating thread.

Fittings 21 and 26 are releaseably locked together by means of connector sleeves 31, each of which comprises a generally cylindrical body 32 having internal threads 33, 34 formed toward the ends thereof. These threads are of suitable diameter and pitch for mating with threads 23 and 29 of the male and female fittings, respectively. Thus, in the preferred embodiment, threads 34 are of substantially coarser pitch than threads 33. Body 32 is also formed to include a conical seat 36 which serves as a limiting abutment for shoulder 24 when the connector sleeve is mounted on fitting 21. The body of the connector sleeve is also provided with longitudinally extending external ribs 37 to facilitate manual gripping of the sleeve. The length of the connector sleeve is such that when the sleeve is mounted on fitting 21, with shoulder 24 engaging seat 36, fittings 21 and 26 can be drawn into mating relationship by engaging thread 29 with thread 34 and rotating fitting 26 through an angle less than 360° and preferably on the order of 180°.

In the preferred embodiment, Luer fittings 21, 26 and connector sleeve 31 are all moulded of a suitable plastic, such as polysulfone or a polycarbonate such as Lexan.

In one preferred use, connector sleeve 31 is threaded onto the male Luer fitting 21 until shoulder 24 engages seat 26. Thereafter, female Luer fitting 26 can be connected to the male Luer fitting simply be engaging thread 29 with thread 34 and rotating the female fitting in the proper direction to draw tip 22 and bore 28 into engagement. Removal of the fitting is effected by rotating it in the opposite direction. The interruption in thread 29 and the coarse pitch of threads 29 and 34 provide what is commonly referred to as a "quick connect" or a "quick disconnect" action for the female fitting.

The invention has a number of important features and advantages. It provides a locking connection between male and female Luer fittings, in which a quick twist of the female fitting will connect or separate the parts. The connector is fully removable, and this results in a very flexible and versatile system in that it enables many types of fittings to be utilized together. In addition, the connector is economical to manufacture and can be utilized with disposable appliances. Moreover, by keeping the connector in place on the male fitting of the appliance and disconnecting the female fitting from the connector, wearing of Luer threads which may be made a part of the appliance threads is effectively eliminated. This is particularly advantageous with manifolds and other appliances made of plastic in that it minimizes the wearing of plastic parts and prolongs the life of the manifold or appliance, thereby conserving the material of which the manifold or appliance is made.

It is apparent from the foregoing that a new and improved connector for Luer fittings has been provided. While only one preferred embodiment has been described, as will be apprent to those familiar with the art, certain changes and modifications can be made without departing from the scope of the invention as defined by the following claims.

What is claimed is:

1. In apparatus for interconnecting medical appliances: a male Luer fitting having a body with an axially extending tapered portion and an external thread of a first pitch on the body toward the base of the tapered portion, a female Luer fitting having an axially extending tapered bore receiving the tapered portion of the male fitting and an external thread of a second pitch, and a connector sleeve removably mounted on the male fitting and having internal threads of the first and second pitches engaging the corresponding threads on the Luer fittings.

2. The apparatus of claim 1 wherein the thread on the female fitting is an interrupted thread of substantially coarser pitch than the thread on the male fitting and the thread in the sleeve engaged by the female fitting is a continuous uninterrupted thread.

3. The apparatus of claim 1 wherein the connector sleeve is provided with longitudinally extending external ribs to facilitate gripping of the sleeve.

4. A removable locking connector for Luer fittings comprising: a generally cylindrical body, an internal thread of a first pitch formed in the body toward one end thereof for engaging a corresponding thread on a first Luer fitting, and an internal thread of a second pitch coarser than the first pitch formed in the body toward a second end thereof for engaging an interrupted thread on a second Luer fitting and drawing the second fitting into mating relationship with the first fitting upon less than 360° of relative rotation between the second fitting and the body of the connector, said connector being readily removable from both the first fitting and the second fitting.

5. The connector of claim 4 wherein the body is provided with longitudinally extending external ribs to facilitate gripping of the connector.

6. In combination: a medical appliance having a male Luer fitting comprising a body portion having an axially extending tapered portion and an external thread of a first pitch on the body portion toward the base of the tapered portion, a connector sleeve removably mounted on the male fitting and having first and second uninterrupted internal threads toward the ends thereof, the first thread engaging the thread on the male fitting and the second thread being of coarser pitch than the first thread, and a female Luer fitting having an axially extending tapered bore and an interrupted external thread engageable with the second thread on the connector sleeve for drawing the tapered portion and the bore into mating relationship upon less than 360° rotation of the female fitting relative to the connector sleeve.

* * * * *